United States Patent [19]

Sanders et al.

[11] Patent Number: 5,800,556
[45] Date of Patent: Sep. 1, 1998

[54] ADJUSTABLE BIPOLAR-UNIPOLAR ADAPTOR FOR A HEAD TRIAL

[75] Inventors: Anthony Sanders, Lakeville; Paul Salvas, Norton; Mark A. Manasas, South Easton, all of Mass.

[73] Assignee: Johnson & Johnson Professional, Inc., Raynham, Mass.

[21] Appl. No.: 652,764

[22] Filed: May 23, 1996

[51] Int. Cl.$^6$ ........................................... A61F 2/76
[52] U.S. Cl. ............................... 623/23; 606/81; 606/89; 606/102
[58] Field of Search ........................ 623/18, 22, 23, 623/66; 606/89, 91, 102, 81

[56] References Cited

U.S. PATENT DOCUMENTS

| | | | |
|---|---|---|---|
| 5,156,624 | 10/1992 | Barnes | 623/18 |
| 5,156,626 | 10/1992 | Broderick et al. | 623/22 |
| 5,358,524 | 10/1994 | Richelsoph | 623/18 |
| 5,405,394 | 4/1995 | Davidson | 623/23 |
| 5,569,263 | 10/1996 | Hein | 606/102 |
| 5,645,607 | 7/1997 | Hickey | 623/23 |

Primary Examiner—John G. Weiss
Assistant Examiner—Bruce E. Snow

[57] ABSTRACT

An adaptor is provided to convert a bipolar shell trial to and from a unipolar head trial adaptor. A preferred embodiment provides a spring-loaded, snap-in adaptor and a neck length adjusting mechanism for a trial system.

9 Claims, 4 Drawing Sheets

ADJUSTABLE BIPOLAR-UNIPOLAR ADAPTOR FOR A HEAD TRIAL

FIELD OF THE INVENTION

The present invention relates to an adaptor for converting a bipolar shell trial into a unipolar head trial and an adaptor for providing adjustable neck lengths on a head trial.

BACKGROUND OF THE INVENTION

In procedures presently used to implant a bipolar hip prosthesis, a trial reduction procedure is typically performed utilizing a four piece system. This system includes a femoral broach trial, a neck portion attached to the broach, a head trial attached to the neck, and a shell for receiving the head trial and fitting within the acetabulum of a patient. The trial procedure using these four pieces can be at times cumbersome for the physician because the head can tend to dislocate and move out of the shell when the physician is attempting to place the trial into position.

Unipolar trial counterpart pieces could be used in some situations to perform the trial reduction of bipolar hip implants because one of the primary interests in performing a trial reduction in both bipolar and unipolar implant procedures is to determine device fit (i.e., shell or head) in the acetabulum. Also, in many cases, the range of motion of the bipolar implant can be approximated with a unipolar trial. The unipolar trial systems used in implanting unipolar hips typically comprise a broach, neck, and head trial.

It is desirable to provide a system for bipolar or unipolar trial reductions that is more efficient and less cumbersome to the surgeon.

It is also desirable to provide a trial system in which fewer components are required and which will save time, money and space in the operating room.

SUMMARY OF THE INVENTION

Accordingly, the present invention provides a bipolar to unipolar head trial adaptor that may be inserted into or removed from a bipolar shell to convert the bipolar shell trial into or from a unipolar head. The adaptor further provides an adjustable neck that eliminates the necessity for multiple unipolar head trials corresponding to different neck lengths for each of the different possible head sizes.

A preferred embodiment provides a spring loaded snap-in adaptor and a quick release neck length adjusting mechanism.

DETAILED DESCRIPTION OF THE DRAWINGS

DETAILED DESCRIPTION OF THE INVENTION

Figure 1:
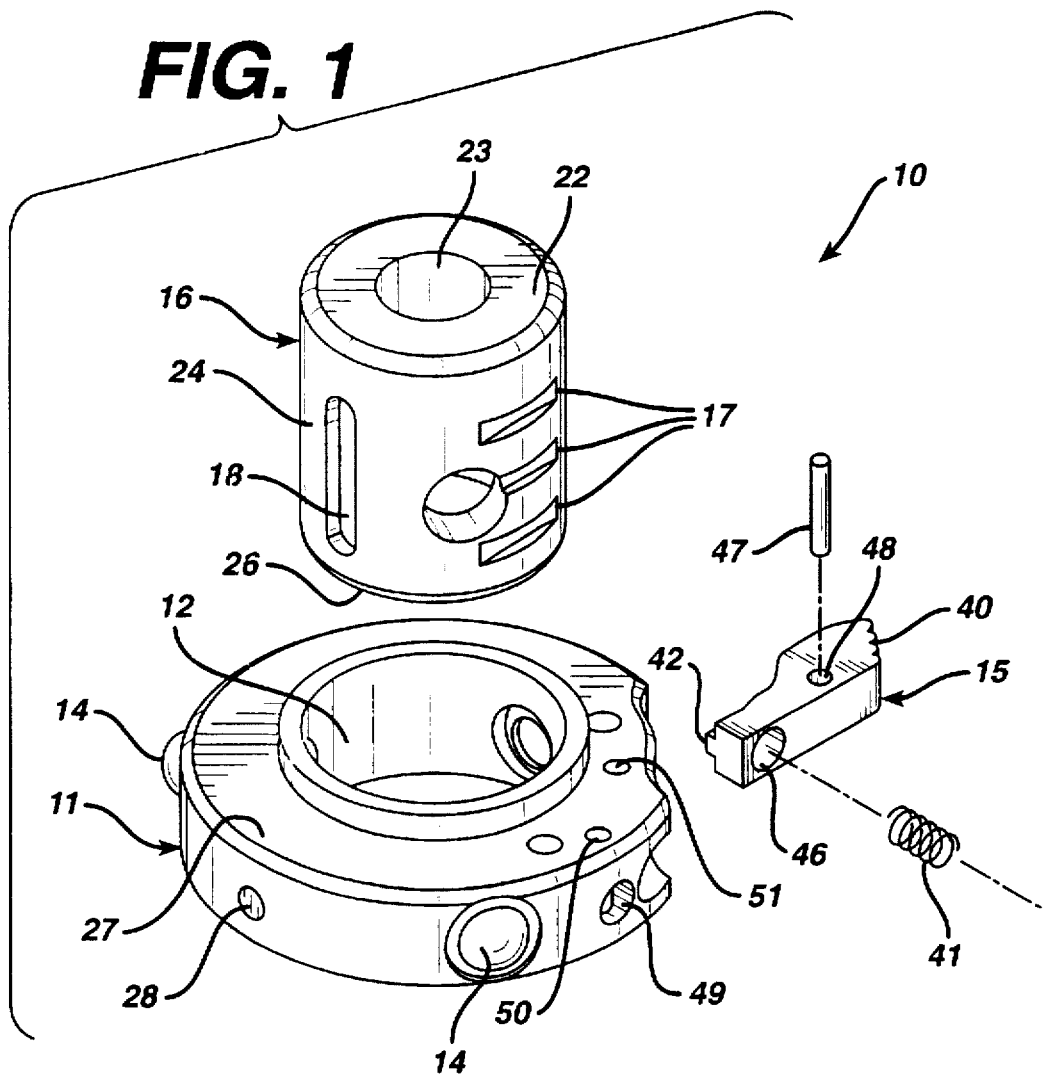
FIG. 1 illustrates an exploded perspective view of the trial adaptor of the present invention.
Figure 2:
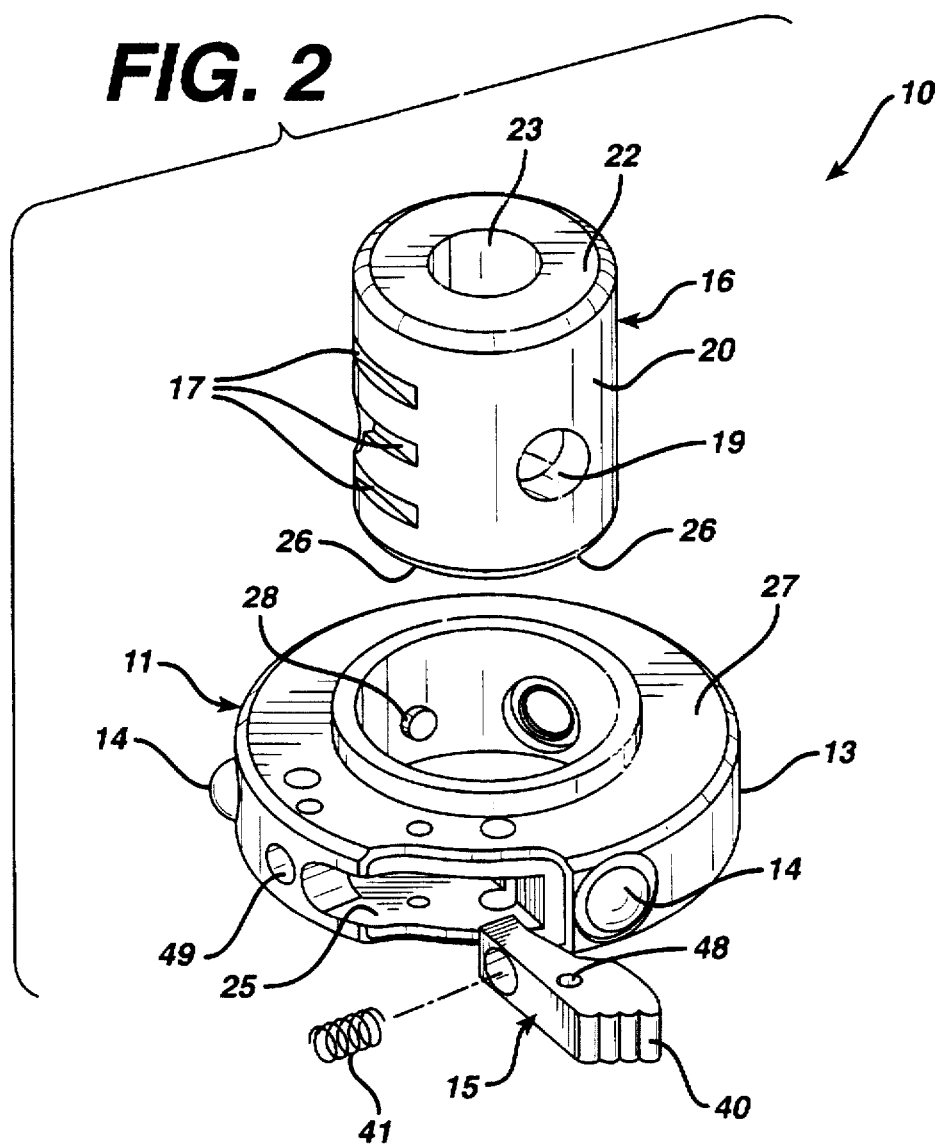
FIG. 2 illustrates an exploded perspective view of the trial adaptor of the FIG. 1 rotated approximately ninety degrees.
Figure 3:
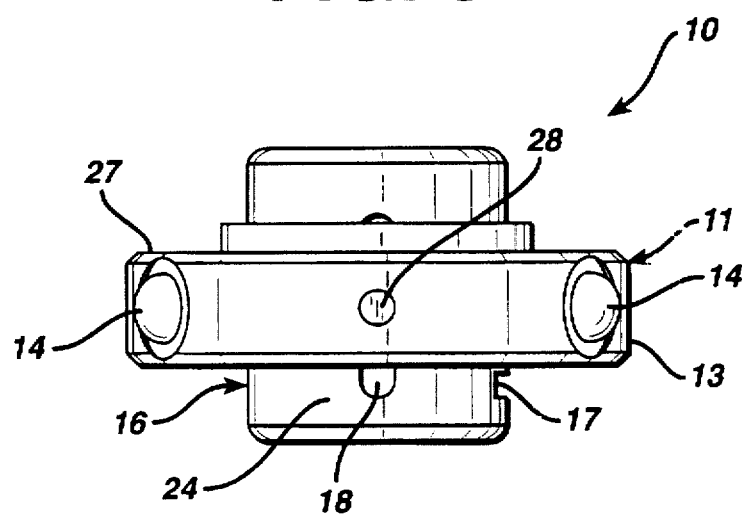
FIG. 3 illustrates a side view of the trial adaptor of the present invention.

Referring now to FIGS. 1 through 5, a trial adaptor 10 is illustrated comprising a cylindrical portion 11 having an opening 12 extending therethrough, spring loaded ball plungers 14 extending from the outer circumference 13 of the cylindrical portion 11 and a pawl 15 extending through the outer circumference 13 of the cylindrical portion 11 partially into opening 12.

Figure 4:
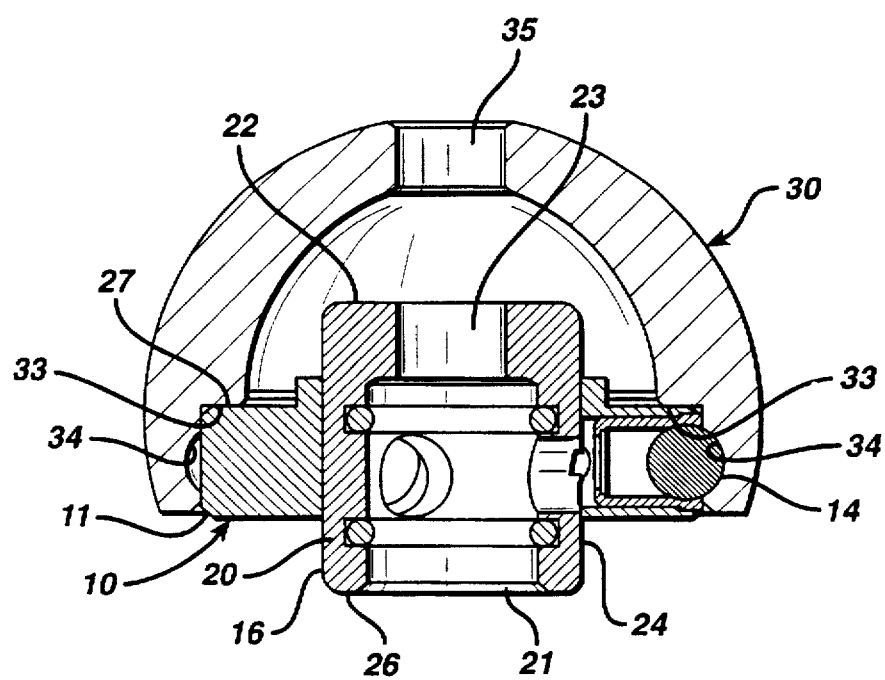
FIG. 4 illustrates a cross sectional view of the trial adaptor of the present invention in use with a bipolar trial shell.
Figure 5:
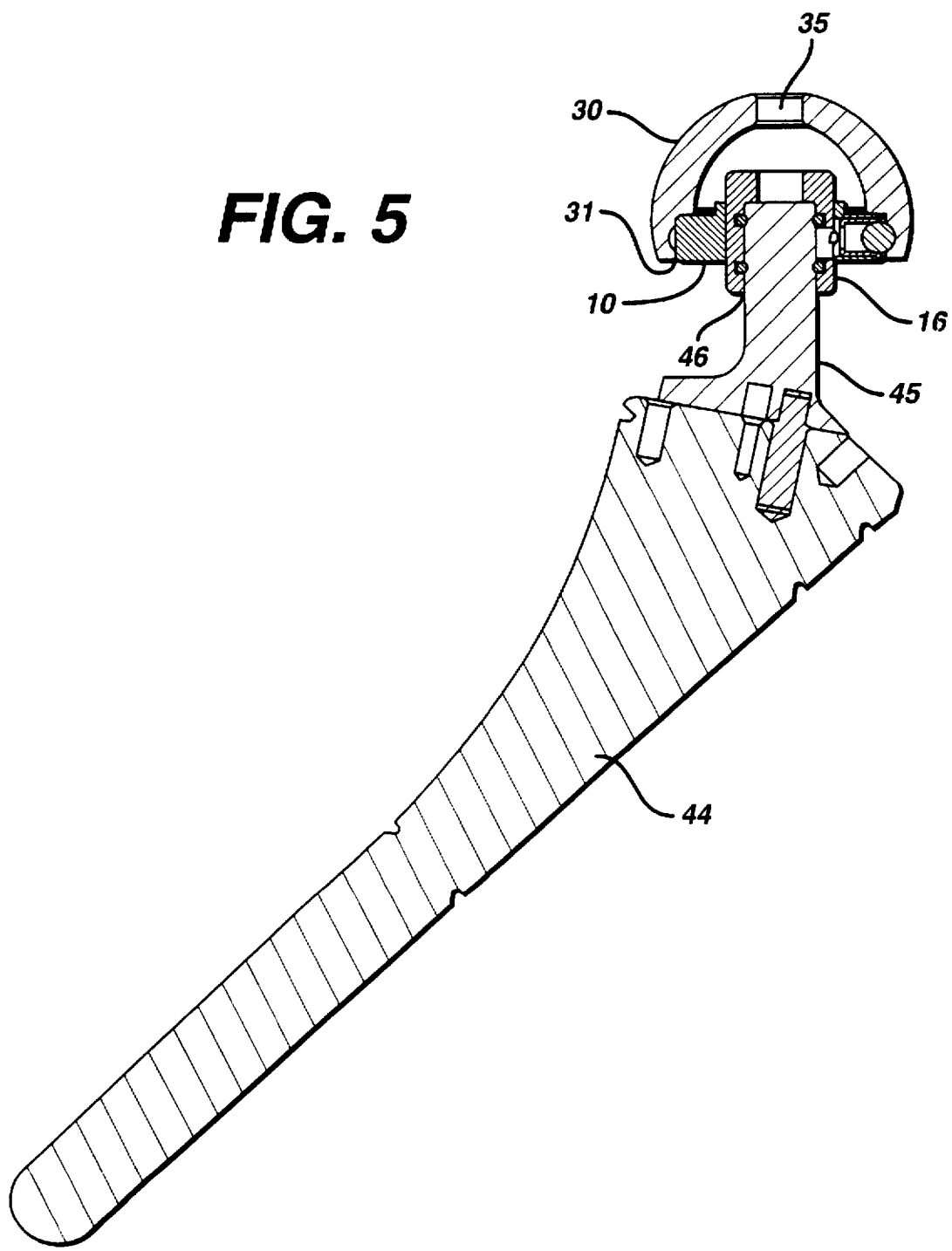
FIG. 5 illustrates a side cross-sectional view of the trial system of the present invention.

The trial adaptor further comprises a barrel 16 which acts as the adjustable neck portion of a unipolar head trial when the adaptor 10 is inserted into a bipolar shell 30 as illustrated in FIG. 4. The barrel 16 comprises three grooves 17 in the outer circumference of the barrel 16. The barrel 16 further comprises a longitudinal slot 18 on the outer circumference 24 of the barrel 16, and openings 19 extending through the cylindrical wall 20 of the barrel. The barrel 16 comprises a longitudinal opening 21 extending from the bottom 26 of the barrel to a top wall 22 of the barrel. The top wall 22 includes a smaller opening 23 continuous with the opening 21..

A dowel pin 28 is press fit through the side of the cylindrical portion 11 and extends into capture slot 18 of barrel 16. The pin 28 movably secures the cylindrical portion 11 to the barrel 16 while the capture slot 18 permits the barrel 16 to move up and down between the three neck length positions defined by the grooves 17.

The pawl 15 comprises a button portion 40, a groove engaging portion 42, and a blind hole 46 for receiving compression spring 41. When assembled the pawl 15 is inserted into the opening 25 and is rotatably coupled to the cylindrical portion 11 with a dowel pin 47 press fit through hole 51 in cylindrical portion 11 and through hole 48 in pawl 15. The compression spring 41 is inserted into the hole 49 in the cylindrical portion 11 and into hole 46 in pawl, aligned with hole 49 of cylindrical portion 11. A dowel pin 50 extends into cylindrical portion 11 across hole 49 to capture the spring 41 in a compressed state in holes 46, 49. The pawl 15 is biased by spring 41 towards the barrel 16 so that when the barrel 16 is in a locked position, the groove engaging portion 42 extends into one of the grooves 17. The button portion 40 is exposed at the outer circumference 13 of the cylindrical portion 11 so that a user may actuate the button 40 to release the engaging portion 42 from engagement with the groove 17 and move the barrel 16 into a desired position.

In use, the cylindrical portion 11 is inserted into an opening 31 in a bipolar shell trial 30 with the barrel 16 extending down from the adaptor 10. The top portion 27 of the cylindrical portion 11 abuts against a shelf 33 within the opening 31 of the shell 30, and spring loaded ball plungers 14 fit into cavities 34 formed within the bipolar trial shell 30. Thus, the adaptor may be snapped into place within the bipolar trial shell 30 and held there by spring loaded ball plungers 14 that extend into cavities 34.

The barrel 16 acts as an interface for a femoral neck trunnion 46 of the neck 45 a femoral trial 44. The femoral neck trunnion 46 may be coupled to the adaptor by inserting it into the opening 21 in the barrel 16.

As assembled, the barrel 16 is inserted into the opening 12 of the cylindrical portion 11. The grooves 17 serve to engage with the pawl 15 to lock the barrel 16 into a selected position corresponding to a desired neck length. Thus the adaptor is arranged to extend the neck length of the femoral trial. The three grooves 17 correspond to three different neck lengths, for example, to zero, five and ten millimeter neck lengths.

The button portion 40 of the pawl 15 is activated to release the engaging portion 42 from the groove 17 engaged by the pawl 15. The barrel 16 is extended to a position so that the neck portion 45 of the femoral trial 44 when attached to the barrel 16 will be at a desired length. The button portion 40 is then released causing the pawl 15 to engage the groove 17 adjacent the pawl 15, locking the barrel 16 into the desired position.

The adjustable neck feature may be incorporated into any trial system whether it be a unipolar, bipolar, etc. system. The adjustable neck may be included with an adaptor as described or with any head or neck portion of a trial system.

The unipolar adaptor 10 may be disassembled from the bipolar shell trial 30 by pushing through the shell trial's apical hole 35 with any small diameter cylindrical instrument at hand.

A physician may elect during surgery to convert the bipolar shell trial into a unipolar head by inserting the unipolar trial adaptor 10. This allows the physician to adjust the fit of the head or the bipolar shell and reduce the femur while electing the appropriate neck length without the usual cumbersome bipolar trial system.

The trial system preferably includes various bipolar shell sizes and various femoral stem sizes to allow the surgeon to select the appropriate size while performing a trial reduction.

Although the present invention is described with respect to particular embodiments and features and uses, numerous variations or equivalents are possible without taking away from the spirit or scope of the claimed invention.

We claim:

1. A femoral head trial adaptor for converting a shell trial to a head trial comprising:
   a cylindrical ring portion comprising a central opening, said ring portion adapted to be received by a shell trial;
   a neck portion extending from said opening in said ring portion, said neck portion comprising an opening for receiving a neck trunnion of a femoral stem trial; and
   a connecting portion for securing said ring portion to a said shell trial.

2. The adaptor of claim 1 wherein said connecting portion comprises a spring loaded connecting element to engage a said shell trial, said spring loaded connecting element biased in a shell trial engaging direction.

3. The adaptor of claim 2 wherein said connecting portion comprises a plurality of ball plungers.

4. The adaptor of claim 1 wherein said neck portion comprises an adjustable neck movably coupled to said ring portion, said adjustable neck having a plurality of positions corresponding to a plurality of neck lengths with respect to said ring.

5. A femoral trial system comprising:
   a femoral stem for inserting in a femoral bone cavity;
   a neck coupled to said stem;
   a shell trial for inserting in an acetabulum;
   said shell trial having an opening, and a cavity formed within said opening, defining a spherical surface; and
   an adaptor for converting a shell trial to a head trial, said adaptor comprising;
   a cylindrical ring portion to be received by said opening of said shell said ring portion comprising a central opening;
   a neck portion extending from said opening of said ring portion, said neck portion comprising an opening for receiving said neck of said femoral trial stem; and
   a connecting portion to secure said ring portion to said shell trial.

6. The trial system of claim 5 wherein said connecting portion comprises a spring-loaded coupling element to engage said trial shell, and wherein said trial shell comprises a surface for engaging said coupling element, said spring-loaded coupling element biased in a shell trial engaging direction.

7. The trial system of claim 5 wherein said neck portion comprises an adjustable neck movably coupled to said ring portion; said adjustable neck having a plurality of positions corresponding to a plurality of neck lengths with respect to said ring.

8. The trial system of claim 5 comprising a plurality of shell trials, said plurality of shell trials having a plurality of shell outer diameters.

9. A femoral head trial comprising:
   a head portion comprising a spherical proximal surface and a distal end, and
   an adjustable neck portion extending distally from and being movably coupled to said distal end, said adjustable neck having a plurality of positions corresponding to a plurality of neck lengths and further comprising an opening for receiving a neck trunnion of a femoral stem trial.

* * * * *